United States Patent [19]

Gupta et al.

[11] Patent Number: 5,604,222
[45] Date of Patent: Feb. 18, 1997

[54] METHOD FOR THE PREPARATION OF 2-CHLORO SULFINYL AZETIDINONES

[75] Inventors: Niranjan L. Gupta; Ramanathan Sankaran; Sakina Sitabkhan, all of Bhopal, India

[73] Assignee: Lupin Laboratories, Ltd., Bombay, India

[21] Appl. No.: 173,757

[22] Filed: Dec. 27, 1993

[51] Int. Cl.[6] .................................................. C07D 499/04
[52] U.S. Cl. ........................ 540/218; 540/219; 540/352; 540/358; 540/359
[58] Field of Search ................................ 540/352, 358, 540/359, 218, 219

[56] References Cited

U.S. PATENT DOCUMENTS

| | | | |
|---|---|---|---|
| Re. 31,730 | 11/1984 | Bouzard | 544/30 |
| Re. 33,948 | 6/1992 | Schmidt | 514/194 |
| 3,641,014 | 2/1972 | Murphy | 260/243 |
| 3,665,003 | 5/1972 | Kennedy | 260/243 |
| 3,668,201 | 6/1972 | Gutowski | 260/243 |
| 3,668,202 | 6/1972 | Foster | 260/243 |
| 3,668,203 | 6/1972 | Clark | 260/243 |
| 3,716,533 | 2/1973 | Humber | 260/243 |
| 3,769,277 | 10/1973 | Long | 260/243 |
| 3,775,408 | 11/1973 | Ochial | 260/243 |
| 3,792,995 | 2/1974 | Ochial | 204/72 |
| 3,883,518 | 5/1975 | Ponticello | 260/243 |
| 3,917,587 | 11/1975 | Chauvette | 260/243 |
| 3,917,588 | 11/1975 | Chauvette | 260/243 |
| 3,925,372 | 12/1975 | Chauvette | 260/243 C |
| 3,932,392 | 1/1976 | Johnson | 260/243 |
| 3,932,393 | 1/1976 | Chauvette | 260/243 |
| 3,989,695 | 11/1976 | Scartazzini | 260/243 |
| 4,031,084 | 6/1977 | Kukolja | 260/243 |
| 4,048,162 | 9/1977 | Kukolja | 544/27 |
| 4,052,387 | 10/1977 | Kukolja | 544/22 |
| 4,060,688 | 11/1977 | Chauvette | 544/30 |
| 4,064,343 | 12/1977 | Chauvette | 544/16 |
| 4,068,071 | 1/1978 | Tsushima | 544/19 |
| 4,068,072 | 1/1978 | Tsushima | 544/19 |
| 4,075,203 | 2/1978 | Chou | 544/18 |
| 4,081,440 | 3/1978 | Kukolja | 544/22 X |
| 4,113,940 | 9/1978 | Kamiya | 544/16 |
| 4,115,643 | 9/1978 | Kukolja | 544/16 |
| 4,123,612 | 10/1978 | Gorman | 544/16 |
| 4,147,864 | 4/1979 | Woodward | 544/16 |
| 4,159,272 | 6/1979 | Chou | 260/332 |
| 4,160,085 | 7/1979 | Tsuji | 544/16 |
| 4,160,091 | 7/1979 | Herron | 544/16 |
| 4,165,315 | 8/1979 | Kukolja | 544/18 X |
| 4,165,316 | 8/1979 | Chou | 544/18 X |
| 4,176,231 | 11/1979 | Corfield | 544/16 |
| 4,178,445 | 12/1979 | Takano | 544/30 |
| 4,182,870 | 1/1980 | Bruynes | 544/16 |
| 4,190,724 | 2/1980 | Chou | 544/16 |
| 4,208,515 | 6/1980 | Chauvette | 544/16 |
| 4,211,702 | 9/1980 | Hatfield | 260/239 |
| 4,223,133 | 9/1980 | Bunnell | 544/16 |
| 4,226,986 | 10/1980 | Hatfield | 544/16 |
| 4,230,620 | 10/1980 | Chou | 260/239.1 |
| 4,240,988 | 12/1980 | Bingham, Jr. | 260/989 |
| 4,252,950 | 2/1981 | Chauvette | 544/16 |
| 4,252,973 | 2/1981 | Slusarchyk | 544/21 |
| 4,254,029 | 3/1981 | Kaspi | 260/239 |
| 4,255,328 | 3/1981 | Woodward | 260/239 |
| 4,260,745 | 4/1981 | Chauvette | 544/16 |
| 4,271,305 | 6/1981 | Hatfield | 548/153 |
| 4,275,062 | 6/1981 | Brever | 424/246 |
| 4,281,116 | 7/1981 | Chauvette | 544/16 |
| 4,281,117 | 7/1981 | Chauvette | 544/16 |
| 4,289,695 | 9/1981 | Chou | 544/18 X |
| 4,301,278 | 11/1981 | Woodward | 544/16 |
| 4,301,279 | 11/1981 | Scartazzini | 544/16 |
| 4,301,280 | 11/1981 | Corfield | 544/16 |
| 4,304,718 | 12/1981 | Kamiya | 260/245 |
| 4,310,459 | 1/1982 | Cundall | 260/239.1 |
| 4,316,955 | 2/1982 | Abbott | 435/47 |
| 4,319,027 | 3/1982 | Woodward | 544/16 |
| 4,322,347 | 3/1982 | Cundall | 260/239.1 |
| 4,332,722 | 6/1982 | Tsuji | 260/245.4 |
| 4,334,063 | 6/1982 | Spry | 544/28 |

(List continued on next page.)

*Primary Examiner*—Jacqueline Haley
*Attorney, Agent, or Firm*—Ladas & Parry

[57] ABSTRACT

An improved method for the preparation of 2-chloro sulfinyl azetidin-4-one of the formula:

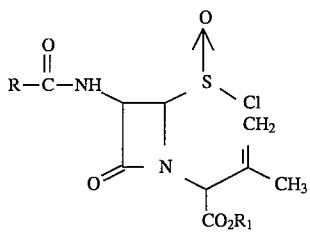

wherein R is: hydrogen; $C_1-C_3$ alkyl; halomethyl; cyanomethyl; phenyl; substituted phenyl; phenoxy, benzyloxy- or substituted benzyl; a group of the formula $R_2$—O—wherein $R_2$ is t-butyl, 2,2,2-trichloroethyl, benzyl or substituted benzyl; a group of the formula $R_3$—(O)$_n$—$CH_2$ wherein $R_3$ is phenyl or substituted phenyl. The 2-chlorosulfinylazetidin-4-one is prepared by reacting a penicillin sulfoxide ester of the general formula

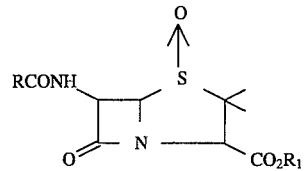

wherein R and $R_1$ have the meanings defined above with an N-chloro halogenating agent in an inert organic solvent. The reaction is carried out in the presence of an acid scavenging amount of a phosphate or hydrogen phosphate of an alkali metal, alkaline earth metal, ammonium, quaternary ammonium or mixtures thereof. These compounds find application as intermediates in the production of cefaclor which are powerful anti-bacterial compounds.

23 Claims, No Drawings

U.S. PATENT DOCUMENTS

| | | | |
|---|---|---|---|
| 4,336,191 | 6/1982 | Kukolja | 260/239 |
| 4,338,436 | 7/1982 | Herron | 544/16 |
| 4,346,218 | 8/1982 | Tsuji | 544/16 |
| 4,354,022 | 10/1982 | Takaya | 544/28 |
| 4,363,807 | 12/1982 | Takaya | 544/16 |
| 4,366,315 | 12/1982 | Bruynes | 544/16 |
| 4,368,156 | 1/1983 | Spitzer | 260/239 |
| 4,368,325 | 1/1983 | Veda | 544/16 |
| 4,374,982 | 2/1983 | Cundall | 544/16 |
| 4,385,176 | 5/1983 | Kamiya | 544/16 |
| 4,389,524 | 6/1983 | Scartazzini | 544/16 |
| 4,405,782 | 9/1983 | Palomo-Coll | 544/21 |
| 4,410,458 | 10/1983 | Kamiya | 260/239.1 |
| 4,431,803 | 2/1984 | Kukolja | 544/16 |
| 4,477,658 | 10/1984 | Scartazzini | 544/16 |
| 4,499,265 | 2/1985 | Torii | 544/16 |
| 4,513,134 | 4/1985 | Kim | 544/16 |
| 4,518,773 | 5/1985 | Cundall | 544/16 |
| 4,558,123 | 12/1985 | McShane | 544/16 |
| 4,591,642 | 5/1986 | Scartazzini | 544/16 |
| 4,623,645 | 11/1986 | Doherty | 514/200 |
| 4,629,542 | 12/1986 | Torii | 204/72 |
| 4,668,781 | 5/1987 | Scartazzini | 540/215 |
| 4,695,627 | 9/1987 | Verweij | 540/224 |
| 4,716,227 | 12/1987 | Furlenmeier | 540/230 |
| 4,767,851 | 8/1988 | Palomo-Coll | 540/218 |
| 4,853,468 | 8/1989 | Torii | 540/215 |
| 4,855,418 | 8/1989 | Cook | 540/205 |
| 4,888,100 | 12/1989 | Hertel | 204/157 |
| 4,921,954 | 5/1990 | Witkamp | 540/222 |
| 4,927,818 | 5/1990 | Takaya | 514/202 |
| 4,950,753 | 8/1990 | Copp | 540/230 |
| 4,958,018 | 9/1990 | Torii | 540/215 |
| 4,968,508 | 11/1990 | Oren | 424/468 |
| 4,985,554 | 1/1991 | Verweij | 540/215 |
| 4,994,454 | 2/1991 | Verweij | 540/215 |
| 5,015,725 | 5/1991 | Scoggins | 528/310 |
| 5,051,406 | 9/1991 | Satoh | 514/21 |
| 5,053,501 | 10/1991 | Kapur | 540/218 |
| 5,066,797 | 11/1991 | Baldwin | 540/215 |
| 5,070,195 | 12/1991 | Khanna | 540/218 |
| 5,095,107 | 3/1992 | Blanchard | 540/205 |
| 5,109,132 | 4/1992 | Verweij | 540/230 |
| 5,126,446 | 6/1992 | Brown | 540/230 |
| 5,132,419 | 7/1992 | Lanz | 540/215 |
| 5,142,043 | 8/1992 | Schreiber | 540/230 |
| 5,159,071 | 10/1992 | Khanna | 540/215 |
| 5,162,522 | 10/1992 | Naito | 540/230 |
| 5,204,458 | 4/1993 | Torii | 540/222 |
| 5,229,509 | 7/1993 | Elvira | 540/218 |
| 5,246,926 | 9/1993 | Bateson | 514/202 |
| 5,250,525 | 10/1993 | Kovacevic | 514/210 |
| 5,254,680 | 10/1993 | Alpeglani | 540/230 |
| 5,302,713 | 4/1994 | Yeh | 540/230 |
| 5,347,000 | 9/1994 | Khanna | 540/218 |
| 5,350,845 | 9/1994 | Brown, Jr. | 540/215 |

METHOD FOR THE PREPARATION OF 2-CHLORO SULFINYL AZETIDINONES

The present invention relates to an improved method for the preparation of 2-chloro sulfinyl azetidinones. More particularly, the invention relates to an improved method for the preparation of 2-chloro sulfinyl azetidin-4-one by the reaction of a penicillin sulfoxide ester with an N-chloro halogenating agent. This method is considerably less expensive than methods of the prior art.

The resulting product 2-chloro sulfinyl azetidin-4-one constitutes an important intermediate in the production of 3-exomethylene cepham carboxylate-1-oxides. The latter, on further elaboration, yield 3-chloro-cephem carboxylates such as cefaclor which are powerful anti-bacterial compounds that find use in pharmaceutical formulations.

BACKGROUND OF THE INVENTION

The basic problem with prior art processes for the preparation of 2-chloro sulfinyl azetidinones from the reaction of a penicillin sulfoxide ester and an N-chloro halogenating agent resides in the unavoidable production at the elevated temperature of the reaction of large amounts of hydrochloric acid. The presence of the generated hydrochloric acid affects adversely the yield of the end product. In fact, if the hydrochloric acid is allowed to remain in the reaction medium, the azetidinone yield decreases considerably. It has, therefore, been the object of manufacturers to provide ways whereby the hydrochloric acid generated is neutralised.

Prior U.S. Pat. Nos. 4,052,387 and 4,081,440 disclose processes for the preparation of 2-chloro sulfinyl azetidine-4-one by the treatment of the corresponding penicillin sulfoxide ester with an N-chloro halogenating agent in an inert solvent, the reaction being carried out in the presence (or absence) of an alkene oxide acid scavenger such as propylene oxide or butylene oxide to remove any hydrochloric acid formed during the reaction. Unfortunately, the subsequent conversion of 2-chloro sulfinyl azetidin-4-one to 3-chloro-cephem carboxylate is exceedingly poor being only in the range of 25% to 40%.

U.S. Pat. No. 4,165,315 discloses a method similar to that of the two above-mentioned U.S. patents.

U.S. Pat. Nos. 4,075,203 and 4,165,316 disclose the employment of a combination of alkylene oxide and calcium oxide as a hydrochloric acid scavenger in the reaction of a penicillin sulfoxide ester with an N-chloro halogenating agent to produce 2-chloro sulfinyl azctidin-4-one.

U.S. Pat. No. 4,289,695 discloses the use of a weakly basic, organic solvent-insoluble poly-4-vinyl pyridine polymer partially cross-linked with divinylbenzene as the hydrogen chloride acceptor in the ring-opening reaction for the conversion of a penicillin sulfoxide ester to 2-chloro sulfinyl azetidin-4-one. The product thus produced on reaction with a Lewis acid gives the corresponding 3-exomethylene cepham sulfoxide ester in a yield of from 10% to 76%. Unfortunately, poly-4-vinyl pyridine polymer is costly and for economic consideration, the hydrochloride produced therefrom requires regeneration to the original base for re-use which makes the entire operation extremely lengthy.

Finally, U.S. Pat. No. 5,070,195 discloses a similar process for the preparation of 2-chloro sulfinyl azetidin-4-one employing anion exchange resins as the acid trapping agent. These resins are shown to have the following structures:

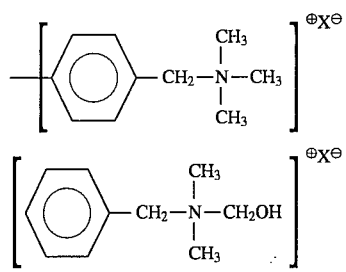

wherein X is a chloride, hydroxide or sulfate ion.

However, unless the hydrochloric acid generated during the reaction is simply adsorbed by the anion exchange resins, it is difficult to rationalise how such acid can be trapped by means of quaternary ammonium functionality since that would be equivalent to the reaction of quaternary ammonium chloride or sulphate with hydrochloric acid. It is, therefore, not surprising that poor yields of 2-chloro sulfinyl azetidin-4-one are obtained when anion exchange polymeric quaternary ammonium compounds are used as acid trapping agents according to U.S. Pat. No. 5,070,195.

SUMMARY OF THE INVENTION

The principal object of the present invention is the provision of a cost-effective, practically viable method for the preparation of 2-chloro sulfinyl azetidin-4-one from the reaction of a penicillin sulfoxide ester with an N-chloro halogenating agent in which the hydrochloric acid generated is effectively, cheaply yet efficiently neutralised to provide the desired product in enhanced yields.

A more specific object of the invention is the provision with the above-mentioned method of an acid-neutralising agent or scavenger which while effectively neutralising generated hydrochloric acid, takes no part in the essential reaction for the production of 2-chloro sulfinyl azetidin-4-one.

A still more specific object is the provision as acid neutralising agent in the above-mentioned method of the phosphates or hydrogen phosphates of ammonia or amines or of metals or substances the oxides and/or hydroxides of which are at least moderately basic in character.

DETAILED DESCRIPTION OF THE INVENTION

The present invention is based on the principle that a stronger acid will displace a weaker acid. It thus relies on the ability of phosphates or hydrogen phosphates of the metals or substances in question to react with the hydrochloric acid generated in the course of the essential reaction of a penicillin sulfoxide ester with an N-chloro halogenating agent and produce inorganic chlorides. This reaction leaves the essential reaction unaffected. Neither the starting phosphates or hydrogen phosphates nor the resulting inorganic chlorides interfere in any way with the production of 2-chloro sulfinyl azetidin-4-one.

A specific example of such a scavenging reaction can be represented as follows:

$$Na_2HPO_4 + HCl \rightarrow NaH_2PO_4 + NaCl$$

Accordingly, the present invention provides an improved method for the preparation of 2-chloro sulfinyl azetidin-4-one of the general formula:

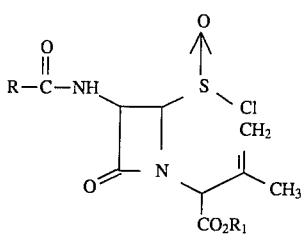

wherein R is:

hydrogen; $C_1$-$C_3$ alkyl; halomethyl; cyanomethyl:

phenyl, substituted phenyl, phenoxy, benzyloxy or substituted benzyl with the substituent group selected from halo, alkyl, alkoxy, protected hydroxy, nitro, cyano and trifluoromethyl;

a group of the formula $R_2$—O— wherein $R_2$ is t-butyl, 2,2,2-trichloroethyl, benzyl or substituted benzyl;

a group of the formula $R_3$—(O)$_n$—$CH_2$ wherein $R_3$ is phenyl or substituted phenyl with the substituent group selected from halo, alkyl, alkoxy, protected hydroxy, nitro, cyano or trifluoromethyl, 2-thienyl, 3-thienyl, 2-furyl, 3-furyl or 1,4-cyclohexadienyl, and n is 0 or 1; or a substituted aryl alkyl group of of formula

wherein $R_4$ has the same meaning as $R_3$ defined above and W is a protected hydroxy or protected amino group; and $R_1$ is a carboxylic acid protecting group selected from the group consisting or $C_1$-$C_4$ allkyl, 2,2,2-trihalo alkyl, benzyl, substituted benzyl, like p-nitrobenzyl, phenacyl, halo substituted phenacyl and benzhydryl, which comprises reacting a penicillin sulfoxide ester of the general formula

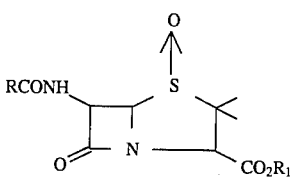

wherein R and $R_1$ have the meanings defined herein with an N-chloro halogenating agent in an inert organic solvent at a temperature of from 70° C. to 150° C. the reaction being conducted in the presence or an acid scavenging amount of a phosphate or hydrogen phosphate of an alkali metal, alkaline earth metal, ammonium, quaternary ammonium or mixtures of any thereof.

Specific examples of the carboxylic acid protecting groups constituting $R_1$ in the above-mentioned formulae include methyl, ethyl, n-propyl, isopropyl, n-butyl, isobutyl, sec-butyl, t-butyl, 2,2,2-trichloroethyl, 2,2,2-tribromoethyl, benzyl, p-nitrobenzyl, p-methoxybenzyl, benzhydryl, phenacyl, p-chlorophenacyl and p-bromophenacyl. Particularly, preferred carboxylic acid protecting groups are methyl, benzyl, p-nitrobenzyl, p-methoxybenzyl, benzhydryl and 2,2,2-trichloroethyl.

The phosphates or hydrogen phosphates constituting the acid scavenging agent of the present invention include the orthophosphates, metaphosphates and polyphosphates of the metals mentioned.

When such phosphates are alkali metal phosphates, the preferred alkali metal is selected from lithium, sodium, potassium and cesium.

When such phosphates are alkaline earth metal phosphates, the preferred alkaline earth metal is selected from magnesium, calcium, strontium and barium.

When the acid scavenging agent is an ammonium phosphate or quaternary ammonium phosphate preferred examples thereof include alkali ammonium phosphates and aryl ammonium phosphates. Such quaternary ammonium phosphates and quaternary ammonium hydrogen phosphates can be represented by one or other of the following structures:

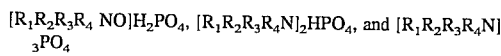

$[R_1R_2R_3R_4 NO]H_2PO_4$, $[R_1R_2R_3R_4N]_2HPO_4$, and $[R_1R_2R_3R_4N]_3PO_4$ wherein each of $R_1$, $R_2$, $R_3$ and $R_4$ is hydrogen, an alkyl group, benzyl or substituted benzyl. Preferred alkyl groups are methyl, ethyl and butyl.

Other phosphates which can be employed as acid scavenging agents include double phosphates of the metals mentioned. An example of such double phosphate is calcium ammonium phosphate.

Of the phosphates and hydrogen phosphates employable as acid scavenging agents in the process of the present invention, the most preferred are phosphates and hydrogen phosphates of sodium, potassium, calcium and barium employed singly or in any combination. Specific phosphates include $NaH_2PO_4$.

As stated above, the criterion for selection of the phosphate scavenging agent is that such phosphates or hydrogen phosphates should be derived from metals or groups the oxides and hydroxides of which are at least moderately, but preferably strongly, basic. Such phosphates are cheap and easily available commercially and many of them are used as commodity chemicals.

Examples of the N-chloro halogenating agents employed in the process of the invention include N-chloro urea, N-chloro amide, N-chloro urethane, N-chloro sulfonamide, N-chlorosulfinimlde, N-ehloroimide, N-chloro succinimide and N-chlorophthalimide.

A feature of the N-chlorohalogenating agent is that its general structure has the N-chloro moiety attached to a strong electron-withdrawing group. This enables easy decomposition of the nitrogen-chlorine bond to provide a chlorine radical in accordance with the following scheme:

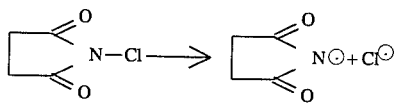

The N-chlorohalogenating agent can be identified by any of the following structures:

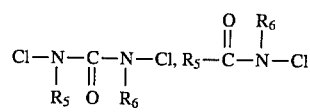

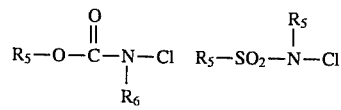

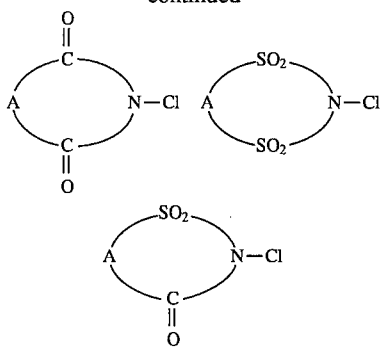

wherein each of $R_5$ and $R_6$ is alkyl, aryl, alkaryl, or a suitably substituted halo, nitro or methoxy group and A is O-phenylene or a $-(CH_2)-_n$ group wherein n is 2 or 3.

The solvent employed for the reaction of the present invention can be selected from the group consisting of benzene, toluene, cyclohexane, n-hexane, ethyl benzene, xylene, mesitylene, dichloromethane, diphenyl ether, tetrahydrofuran, carbon tetrachloride, chloroform, 1,1,2-trichloroethane or any aprotic solvent which does not react with either the starting reactants or the resultant product of the reaction.

A particularly suitable range of temperature for the reaction of the inventive process is from 100° C. to 115° C.

According to a preferred feature of the invention, the molar ratio between the reactants, i.e. the penicillin sulfide ester and the N-chloro halogenating agent is maintained between 1 and 1.5. The reaction is conveniently conducted in an excess of N-chlorohalogenating agent of from 10% to 30%.

Since the reaction path for generation of hydrochloric acid is not known, the molar ratio of the N-chlorohalogenating agent and the acid scavenging agent can vary. Best yields of the desired 2-chloro sulfinyl azetidin-4-one were achieved when the molar ratio of the N-chlorohalogenating agent to the acid scavenging agent varied between 0.3 and 15. The most preferred molar ratio range was from 10 to 13.

The acid scavenging phosphates or hydrogen phosphates and the inorganic chlorides produced as a result of the reaction of such phosphates with hydrochloric acid liberated during the ring-opening reaction are insoluble in the reaction medium. Accordingly, the phosphates and the produced inorganic chlorides are easily filtered off.

Furthermore, the acid scavenging phosphates do not induce any side reaction detrimental to the efficiency of the essential 2-chloro sulfinyl azetidin-4-ones produced. This fact has been round to contribute to improve yields or from 70% to 90% of 3-chloro-cephem carboxylates when the 2-chloro sulfinyl azetidin-4-ones resulting from the reaction are cyclized with a Friedel-Crafts catalyst such an a Lewis acid to form said carboxylates.

The invention also provides a process for the synthesis of a 3-exomethylene cepham sulfoxide ester or the general formula:

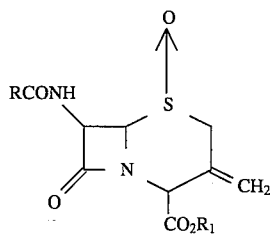

wherein R is:

hydrogen; $C_1-C_3$ alkyl; halomethyl: cyanomethyl:

phenyl, substituted phenyl, phenoxy, benzyloxy or substituted benzyl with substituent group selected from halo, alkyl, alkoxy, protected hydroxy, nitro, cyano and trifluoromethyl:

a group of formula $R_2-O-$ wherein $R_2$ is t-butyl, 2,2,2-tri-chloroethyl, benzyl or substituted benzyl;

a group of formula $R_3-(O)-N-CH_2$ wherein $R_3$ is phenyl or substituted phenyl with the substituent group selected from halo, alkyl, alkoxy, protected hydroxy, nitro, cyano and trifluoromethyl, 2-thienyl, 3-thienyl, 2-furyl, 3-furyl or 1,4-cyclohexadienyl, and n is 0 or 1; or a substituted aryl alkyl group of of formula $R_4$ $$-\underset{W}{\overset{}{\underset{|}{CH}}}-$$

wherein $R_4$ has the same meaning as $R_3$ defined above and W is a protected hydroxy or protected amino group: and $R_1$ is a carboxylic acid protecting group selected from the group consisting of $C_1-C_4$ alkyl, 2,2,2-trihalo alkyl, benzyl, substituted benzyl, like p-nitrobenzyl, phenacyl, halo substituted phenacyl and benzhydryl, which comprises reacting a penicillin sulfoxide ester of the general formula

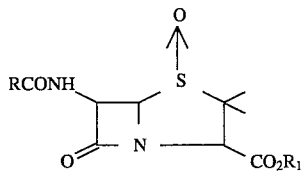

wherein R and $R_1$ have the meanings defined herein with an N-chloro halogenating agent in an inert organic solvent at a temperature of from 70° C. to 150° C., the reaction being conducted in the presence of an acid scavenging amount of a phosphate or hydrogen phosphate of an alkali metal, alkaline earth metal, ammonium, quaternary ammonium or mixtures of any thereof, recovering the 2-chloro sulfinyl azetidin-4-one thus prepared and cyclizing it by methods known per se to synthesise the desired 3-exomethylene cepham sulfoxide ester.

Most conveniently, cyclization of the recovered 2-chloro sulfinyl azetidin-4-one is effected by reacting the recovered compound with a Friedel-Crafts catalyst. The Friedel-Crafts catalyst is preferably a Lewis acid selected from stannic chloride, ferric chloride and zinc chloride.

The invention will now be described more explicitly in the Examples that follow in which Example 1 is presented as a comparative or reference example to illustrate the decline in yield of cyclized 3-exomethylene sulfoxide ester when no acid scavenging agent is employed during the intermediate stage of the preparation of the 2-chloro sulfinyl azetidin-4-one.

EXAMPLE I 3-exo methylene cepham-4-carboxylate-1-oxide with no acid scavenging agent employed during the ring opening reaction Toluene (300 ml) was binary distilled under a Dean Stark water trap until 80 ml of liquid was removed from the trap. 10 g of p-nitrobenzyl-6-phenoxyacetamido 2,2-dimethyl penam-3-carboxylate-1-oxide and 5 g of N-chlorophthalimide were added. The mixture was refluxed for 90 m. The reaction mixture was found to have a pH of 3.5 and had turned dark brown in colour. The reaction mixture was cooled to 0° C. and the filtrate was added to 7.7 g of stannic chloride in toluene at 0° C. The resulting red coloured complex was stirred for 16 hours at ambient temperature and filtered. The complex was dissolved in ethyl acetate, washed with water, dried over $MgSO_4$ and concentrated under vacuo to give 2.5 g (25%) of the corresponding 3-exo methylene cepham-4-carboxylate-1-oxide; mt. pt. 192° C. to 139° C.

EXAMPLE 2 p-nitrobenzyl-3-methyl-2-(2-chlorosulfinyl-4-oxo-3-phenoxy acetamido-1-azetidinyl)-3-butenoate Toluene 300 ml was distilled under a Dean Stark water trap till 80 ml of liquid was removed. 2.9 g of disodium hydrogen orthophosphate, 10 g of p-Nitrobenzyl 6-phenoxy acetamido penam-3-carboxylate-1-oxide and 5.0 g of N-chlorophthalimide were added. The suspension was heated at the reflux temperature for 160 minutes. The pH of the reaction mixture at 30° C. was found to be 7.8. The reaction mass was then cooled in an ice-bath for about 20 min. The cold suspension was filtered to remove insoluble material and the filtrate was concentrated under vacuo to dryness to provide 10.35 g (96.9%) of the title compound.

IR (KBr) $cm^{-1}$: 1790, 1740, 1690, 1600, 1520, 1495, 1350, 1240, 1180, 1080.

$^1$HNMR ($CDCl_3$): Delta 1.93 ($s_1$3H), 4.53 (s,2H), 5.05 (bs, 1H), 5.23 (m,2H), 5.33 (s,2H), 5.57 (d, 1H), J=4.5Hz), 6.18 (dd, 1H, J=4.5Hz), 6.9–8.1 (m, 9H, Ar).

EXAMPLE 3 p-nitrobenzyl-3-methyl-2-(2-chlorosulfinyl-4-oxo-3-phenoxy acetamido-1-azetidinyl)-3-butenoate A solution of 10 g of p-nitrobenzyl-6-phenoxyacetamido-2, 2-dimethyl penam-3-carboxylate-1-oxide and 3.7 g of N-chloro succinimide in 400 ml of dry toluene containing 15 g of disodium hydrogen orthophosphate was refluxed for 100 minutes. The mixture was cooled and filtered and evaporated in vacuo to dryness to provide the product p-nitrobenzyl-3-methyl-(2-chlorosulfinyl -4-oxo-3-phenoxyacetamido-1-azetidinyl)-3-butenoate (contaminated with succinimide) in a yield of 97.0%.

$^1$HNMR: ($CDCl_3$): Delta 1.93 (s,3H), 4.53 (s,2H), 5.05 (bs, 1H), 5.23 (m,2H), 5.33 (s,2H), 5.57 (d, 1H), J=4.5 Hz), 6.18 (dd, 1H, J=4.5Hz), 6.9–8.1 (m, 1H, Ar).

EXAMPLE 4 p-nitrobenzyl-3-methyl-2-(2-chlorosulfinyl-4-oxo-3-phenoxyacetamido-1-(azetidinyl)-3-butenoate 250 ml of 1,1,2-trichloroethane were heated in equipment containing a Dean Stark water trap to remove azeotropically any moisture present. To the resulting dried 1,1,2-trichloroethane were added 5 g of p-nitrobenzyl-6-phenoxyacetamido 2,2-dimethyl penam-3-carboxylate-1-oxide, 2.0 g of N-chlorosuccinimide and 5 g of calcium hydrogen phosphate. The mixture was then refluxed for 1 hour. A sample of the reaction mixture was withdrawn and the solvent was removed. The product obtained was found by NMR analysis to be consistent with p-nitro-benzyl 3-methyl-2-(2-chlorosulfinyl-4-oxo-3-phenoxy acetamido-1-azetidinyl)-3-butenoate.

$^1$HNMR: Delta 1.93 (S, 3H), 4.53 (S,2H). 5.05 (bs, 1H), 5.23 (m,2H), 5.33 (S,2H) 5.57 (d, 1H J=4.5Hz), 6.18 (dd, 1H, J=4.5Hz) 6.9–8.1 (m, 9H, Ar).

EXAMPLE 5 p-nitrobenzyl-3-methyl-2-(2-chlorosulfinyl-4-oxo-3-phenoxyacetamide-1-azetidinyl)-3-butenoate Toluene (400 ml) was binary distilled under a Dean Stark water trap for removal of moisture. 10 g of diammonium hydrogen phosphate. 10 g of p-nitrobenzyl-6-phenoxy acetamido 2,2-dimethyl penam-3-carboxylate penam -1-oxide and 4.2 g of N-chlorophthalimide were added. The suspension was heated at reflux temperature for 100 minutes and was then cooled in an ice bath for about 20 min. The cold suspension was filtered to remove insoluble material and the filtrate was concentrated under vacuo to dryness to provide 10.75 g (97%) of the compound p-nitrobenzyl-3-methyl-2-(2-chlorosulfinyl-4-oxo-3-phenoxyacetamido-1-azetidinyl)-3-butenoate.

EXAMPLE 6

2,2,2-trichloroethyl-3-methyl-2-[2-chlorosulfinyl-4-oxo-3-(2-thienylacetamido)-1-azetidinyl[-3-butenoate and 2,2,2-trichloroethyl-7-(2-thienylacetamido-3-methylene cepham-4-carboxylate-1-oxide A solution of 3.5 g of disodium hydrogen orthophosphate in 450 ml of toluene was prepared and dried azeotropically by distilling 100 ml of toluene from the mixture. The mixture was cooled and 5 g of 2,2,2-trichloroethyl-6-(2-thienylacetamido)-2,2-dimethyl penam-3-carboxylate-1-oxide and 2 g of the mixture were then refluxed for 100 minutes, cooled and filtered. A 5 ml portion of the refluxed mixture was evaporated in vacuo to dryness to provide 2,2,2-trichloro ethyl -3-methyl-2-[2-chlorosulfinyl-4-oxo-3-(2-thienylacetamido)-1-azetidinyl[-3-butenoate.

NMR($CDCl_3$) Delta 1.87 ($s_1$3, CH ($CH_3$)=$CH_2$), 3.82 ($s_1$2H. Side chain $CH_2$), 4.80 (ABq, 2H, J=13Hz, —$CH_2CCl_3$) 5.18 ($m_1$3H, —CH($CH_3$)=$CH_2$), 5.50 (d, 1, J=4.5Hz, azetidinone $C_2$—H) and 6.05 (m, 1, azetidinone $C_3$—H).

To the remainder of the toluene solution of the sulfinyl chloride were added 2.14 ml of anhydrous stannic chloride. The mixture was subjected to stirring for 8 hours. The complex was filtered washed with hexane and added slowly to 50 ml methyl alcohol at 0° C. The slurry was filtered to yield 3.1 g (62%) of the corresponding cepham-4-carboxylate-1-oxide.

NMR(DMSO-$d_6$) Delta 3.38 (bs, 2H $C_2$—H), 3.80 (s,2H), 5.02 (s,2H, —$CH_2CCl_3$), 5.04 (d, 1H. J=4Hz, $C_6$—H, and 8.16 (d, 1, J-8Hz, —NH).

EXAMPLE 7 p-nitrobenzyl-7-phenoxy acetamido -3-exomethylene cepham -4-carboxylate-1-oxide 400 ml of reagent grade toluene were dried by azeotropic distillation for 1 hour during which 100 ml were discarded. The toluene was allowed to cool and 9.7 g of calcium hydrogen phosphate, 10 g of p-nitrobenzyl-6-phenoxyacetamido-2,2-dimethyl penam-3-carboxylate-1-oxide and 5.4 g of N-chlorophthalimide were added thereto. The reaction flask was equipped with a Dean Stark trap and the mixture was heated for 2 hours. The reaction mixture was cooled to a temperature of about 0° C. and stirred for 15 min at 10° C. The reaction mixture was filtered and NMR of intermediate azetidinone sulfinyl chloride was obtained by withdrawing a small sample of the mixture, evaporating the sample and then reconstituting the residue in deuterated chloroform. The NMR ($CDCl_3$) of the sulfinyl chloride showed the following signals:

Delta 1.93 (S,3H), 4.55 (S,2H) 5.13–55.03 (m,5H), 5.33 (S,2H), 5.57 (d, 1H J=4.5Hz) 6.30 (q, 1H J=4.5Hz) 7.0–6.8 (m, 5H) 7.2 (d, 2H, J=11Hz) and 8.23 (d, 2H J=11Hz).

The reaction mixture was cooled to −5° C. and 9 g of stannic chloride were added over a period of 15 min. at −5° C. The slurry was stirred for 16 hours at 20° C. and filtered. The complex was washed with hexane and added slowly to methanol at 0° C. and stirred for 4 hours at 0° C. The product was filtered, washed with methyl alcohol and dried in vacuo to yield 7.0 g (70%) of the title product melting at 195° C.

EXAMPLE 8 benzhydral-3-methyl-2-(2-chlorosulfinyl-4-oxo-3-phenoxyacetamido-1-azetidinyl)-3-butenoate 1 g of disodium hydrogen orthophoshate was refluxed in 60 ml 1,1,2-trichloroethane and moisture was removed by Dean Stark apparatus. After cooling the mixture to 30° C., 2 g of benzhydral 6-phenoxyacetamido-2,2-dimethyl penam-3-carboxylate-1-oxide and 1 g of N-chloro succinimide were added. The mixture was refluxed for 1.5 hours and then cooled to 10° C. The 2 ml solution was evaporated under vacuo to dryness to provide title sulfinyl chloride.

NMR ($COCl_3$) Delta 1.88 (s,3H), 4.53 (s, 2H) 4.90 (s, 1H) 5.14 (s, 2H) 5.54 (s, 1H) 6.24 (q, 1H), 6.95 (s, 1H), 7.15–7.40 (m, 15H 8.0 (d, 1H).

To the remainder of the toluene solution of the sulfinyl chloride, there were added 0.856 ml of anhydrous stannic chloride. The mixture was stirred for 8 hours. The complex was filtered, washed with hexane and added slowly to 20 ml methyl alcohol at 0° C. and then stirred for 4 hours at 0° C. The slurry was filtered to yield 1.6 g (80%) of the corresponding 3-exomethylene cepham carboxylate-1-oxide.

EXAMPLE 9 p-nitrobenzyl 7-phenoxyacetamido-3-methylenecepham-4-carboxylate-1-oxide

To the sulfinyl chloride obtained from Example 2, dissolved in dry toluene 1.0 ml diethyl ether and 10.7 g stannic chloride in 10 ml dry toluene were added over a period of 40 minutes at −5° C. to −10° C. The mixture was stirred for 40 minutes at −5° C. and for 8 hours at ambient temperature. The light orange complex was filtered, washed with 50 ml hexane and dried on the filter. The dried granular precipitate was then added slowly to 250 ml of methyl alcohol. The suspension was stirred for 4 hours at 0° C. The product was filtered and dried under vacuo to yield 8.0 g of the title product (80%).

$^1$H NMR: Delta 3.70 (ABq, 2H, J=16Hz), 4.54 (s,2H), 4.95 (d, 1H, J=4.5Hz), 5.28 (s, 2H), 5.32 (s, 1H) 5.50 (s, 1H), 5.80 (s, 1H) 5.95–6.14 (dd, 1H, J=4.5Hz), 6.90–8.41 (m, 10H).

m.p.: 193°–194° C.

IR $cm^{-1}$: 3080, 3000, 1780, 1740, 1690, 1600, 1520, 1495, 1440, 1350, 1259, 1190,1060,1020,940,750,690.

Anal. calcd for $C_{23}H_{21}N_3O_8S$ (490.5)

C: 55.31 H: 4.24 N: 8.41 O: 25.62 S: 6.42

Found C: 55.32 H: 4.26 N: 8.42 O: 25.64 S: 6.40

EXAMPLE 10 p-nitrobenzyl 7-phenoxyacetamido-3-methylene cepham 4-carboxylate-1-oxide 1.5 lit. of reagent grade toluene were dried by azeotropic distillation for 2 hours during which 200 ml were discarded. The toluene was allowed to cool and 27 g of disodium hydrogen orthophosphate, 50 g p-nitrobenzyl-6-phenoxyacetamido 2,2-dimethyl penam-3-carboxylate-1-oxide and 27 g of N-chlorophthalimide were added. The reaction flask was equipped with a Dean Stark trap and the mixture was refluxed for 140 min. The reaction mixture was cooled to a temperature of about 10° C. The reaction mixture was then filtered and the filtrate chilled in an ice bath. To the cold filtrate were added consecutively 7.5 ml diethyl ether and 50 g of stannic chloride. The light orange complex which formed was stirred for 30 minutes at ice bath temperature and then at ambient temperature for about 16 hours, filtered and washed with 375 ml of hexane. The washed complex was slowly added to (250 ml) methyl alcohol with formation of a slurry of the product, p-nitrobenzyl-7-phenoxy acetamido-3-exomethylenecepham-4-carboxylate-1-oxide. The slurry was stirred for 4 hours at ice bath temperature, filtered, washed with methyl alcohol and vacuum dried to yield 37.5 g (75%) of off-white title product melting at about 195° C.

EXAMPLE 11 p-nitrobenzyl-7-phenyl acetamido-3-methylene cepham-4-carboxylate-1-oxide 300 ml of reagent grade toluene were dried by binary distillation with the removal of 40 ml of toluene. The distillation was discontinued and 4 g of disodoium hydrogen orthophosphate. 10 g of p-nitrobenzyl 6-phenoxyacetamido, 2,2-dimethyl penam-3-carboxylate-1-oxide and 5.4 g of N-chlorophthalimide were added. The mixture was heated at the reflux temperature for 160 minutes and was then cooled to 0° C. and filtered. The filtrate was cooled to 5° C. and added 2 ml diethyl ether and 10.7 g of stannic chloride were added consecutively thereto. After 40 minutes stirring at 5° C. the light brown coloured complex which formed was stirred overnight at ambient temperature. The complex was filtered and washed with 25 ml of hexane. After addition of the complex in 40 ml methanol at 0° C., the light yellow precipitate separated out. It was stirred for 4 hours at 0° C.

The product was filtered and dried. The yield of the title product was 6.9 g (59%) m.p. 198° C.

EXAMPLE 12 p-nitrobenzyl-7-phenoxyacetamido-3-methylene cepham-4-carboxylate-1-oxide 15 g of disodium hydrogen orthophosphate were suspended in 300 ml 1,1,2 trichloroethane and subjected to azeotropic distillation. The contents were cooled and 10 g of p-nitrobenzyl-6-phenoxy acetamido-2, 2-dimethyl penam-3-carboxylate-1-oxide and 5.0 g of N-chlorophthalimide were added. The reaction proceeded as in Example 11.

Yield of the title product was 7.5 g (75%).

EXAMPLE 13

2,2,2-trichloroethyl-7-phenoxy acetamido-3-exomethylene cepham-4-carboxylate-1-oxide 1 g of disodium hydrogen orthophosphate was suspended in 37 ml toluene and subjected to azeotropic distillation using a Dean Stark water trap. The heat was discontinued and 2 g of 2,2,2-trichloro ethyl-6-phenoxyacetamido-2,2 -dimethyl penam-3-carboxylate-1-oxide and 1.08 g of N-chlorophthalimide were added at room temperature. The reaction mixture was heated at the reflux temperature for 120 minutes and was then cooled to about 10° C. The mixture was filtered, the insoluble material was removed and the filtrate was further cooled to 0° C. 0.38 ml of diethyl ether was added thereto followed by the addition of 1 ml of stannic chloride in 2 ml toluene under stirring. Stirring was continued for 30 minutes at 0° C. and for another 6 hours at room temperature. The complex was filtered and washed with 10 ml hexane and added to 20 ml methanol at 0° C. with stirring. The slurry was filtered to give 1.58 g (80%) of the title product. mm.p. 140° C. to 143° C.

EXAMPLE 14 p -nitrobenzyl -7-phenoxy acetamido-3-exomethylene-cepham-4-carboxylate-1-oxide 400 ml of reagent grade toluene were dried by binary distillation with the removal of 40 ml of toluene. The distillation was discontinued and 5 g of dipotassium hydrogen orthophosphate, 10 g of p-nitrobenzyl-5-phenoxy-acetamido-2,2-dimethylpenam-3-carboxylate-1-oxide and 5.0 g of N-chlorophthalimide were added. The mixture was heated at the reflux temperature for 100 minutes and was then cooled to 0°–5° C. and filtered. The filtrate was cooled to 55° C. and added consecutively 1.5 ml of diethyl ether and 10.7 g of stannic chloride. The brown colored complex formed was stirred for 10 hrs at room temperature. The complex was filtered and washed with hexane. The washed complex (tan sand like) was slurried with 50 ml methyl alcohol. The slurry was stirred for 4 hrs at 0° C. filtered, washed with methyl alcohol and dried in vacuo at ambient temperature to yield 66% of the title product.

EXAMPLE 15 p-nitrobenzyl 7-phenyl acetamido -3-exomethylene cepham-4-carboxylate-1-oxide 2.5 g of dipotassium hydrogen orthophosphate were suspended in 150 ml toluene. Moisture was removed by azeotropic distillation through a Dean Stark water trap. The contents were cooled to 25° C. followed by the addition of 5 g of p-nitrobenzyl-6-phenyl acetamido-2,2-dimethyl penam-3-carboxylate-1-oxide and 2.45 g of N-chloro phthalimide. The reaction mixture was refluxed for 100 m and allowed to cool to 10° C. The insoluble material which separated was removed by filtration. The filtrate was further cooled to 0° C. and 1 ml of diethyl ether was added thereto followed by 2.5 ml of $SnCl_4$. After 60 m stirring at 0° C., the orange-colored complex was kept overnight at 10° C. The complex was filtered and washed with 5 ml hexane. After the addition of the complex in 40 ml methanol at 5° C., the light yellow precipitate separated out. It was stirred for 2 h at 5° C. The product was filtered and dried. Yield of the title product was 4.21 g (80%) m.p. 206° C. to 207° C.

$^1$HNMR ($CDCl_3$) Delta 3.30–3 (M,4H); 5.30 (d. 1H); 5.24 (s, 3H), 5.45 (s, 1H); 5.75 (s, 1H); 6.00 (dd, 1H); 6.90 (d, 1H) and 7.20 to 8.40 (m, 9H).

EXAMPLE 16

2,2,2-trichloroethyl-6-phenoxy acetamido-3-exomethylene cepham-4-carboxylate-1-oxide A solution of 10 g of p-nitrobenzylk-6-phenoxyacetamido-2,2-dimethyl penam-3-carboxylate-1-oxide and 3.7 g of N-chloro succinimide in 400 ml of dry toluene containing 15 g of dipotassium hydrogen orthophosphate was refluxed from 100 m. The mixture was cooled and filtered. The toluene solution of sulfinyl chloride was cooled to 0° C. and tin (IV) chloride in toluene and ether was added. The resultant slurry was allowed to exotherm to 21° C. to 23° C. and was stirred for 16 hours. The slurry was filtered, washed with 25 ml of toluene and returned to the reaction flask with 50 ml methyl alcohol. The slurry was filtered and the light coloured solid was dried in a vacuum oven at 45° C. for 4 hours. The assay corrected isolated yield of 3-methylene-7(phenoxyacetamido) cepham-4-carboxylic acid, 2,2,2 trichloroethyl ester 1-oxide was 71.2% and the purity was determined to be 96.7% by HPLC assay.

EXAMPLE 17 p-nitrobenzyl-7-phenyl acetamido-3-exomethylene cepham-4-carboxylate-1-oxide 400 ml of reagent grade toluene were dried by azeotropic distillation for 1 hour during which 100 ml were discarded. The toluene was allowed to cool and 7.5 g of calcium hydrogen phosphate. 10 g of p-nitrobenzyl-6-phenylacetamido-2,2-dimethyl penam-3-carboxylate-1-oxide and 4.5 g of N-chlorophthalimide were added thereto. The reaction proceeded as in Example 16 to give the final title product exomethylene, in 65% yield m.p.: 208° C.

EXAMPLE 18 p-nitrobenzyl-7-phenoxy acetamido-3-methylene cepham-4-carboxylate-1-oxide

The reaction mixture from Example 17 was cooled in an ice bath and 4.8 g of stannic chloride were added. The mixture was stirred for 8 hours at 20° C. and the stirred again for 4 hours at 0° C.

The product p-nitrobenzyl-7-phenoxyacetamido-3-methylene cepham-4-carboxylate-1-oxide was collected by filtration and dried in vacuo to give a yield of 3.15 g (63%).

EXAMPLE 19 p-nitrobenzyl-7-phenyl acetamido-3-exomethylene cepham carboxylate-1-oxide 5 g of diammonium hydrogen phosphate were suspended in 200 ml of 1,1,2-trichloroethane and subjected to azeotropic distillation. The contents were cooled and 5 g of p-nitrobenzyl-6-phenylacetamido-2,2-dimethylpenam-3-carboxylate-1-oxide and 2.5 g of n-chlorophthalimide were added. The reaction proceeded as in Example 17 yielding 2 g (40%) of the title 3-exomethylene compound.

EXAMPLE 20

2,2,2-trichloro ethyl -7-phenoxy acetamido-3-exomethylene cepham carboxylate-1-oxide 5 g of diammonium hydrogen phosphate were suspended in 200 ml of 1,1,2-trichloroethane and subjected to azeotropic distillation. The contents were cooled and 5 g of 2,2,2-trichloroethyl-6-phenoxyacetamido-2,2-dimethylpenam-3-carboxylate-1-oxide and 1.5 g of N-chloro succinimide were added. The reaction proceeded as in Example 19 to yield in 39% yield (1.95 g) of the title product.

EXAMPLE 21 p-nitrobenzyl-7-phenoxy acetamido -3-exomethylene cepham carboxylate-1-oxide 2.5 g of disodium hydrogen orthophosphate were suspended in 200 ml of toluene and subjected to azeotropic distillation. The contents were cooled and 5 g of p-nitrobenzyl-6-phenoxyacetamido-2,2-dimethyl penam-3-carboxylate-1-oxide 4.25 g of N-chlorophthalimide were added and the mixture refluxed for 100 minutes. The reaction mixture was cooled to 10° C. and filtered. The sulfinyl chloride solution was then added to 7.2 g of stannic chloride in toluene at 0° C. to 5° C. and stirred for 8 hours. The complex was filtered, washed with pentane and slurried with 25 ml methyl alcohol. The slurry was stirred for 4 hours at 0° C. and filtered and dried in vacuo to yield 3.6 g (72%) of exomethylene compound.

We claim:

1. A method for the preparation of 2-chloro sulfinyl azetidin-4-one of the formula:

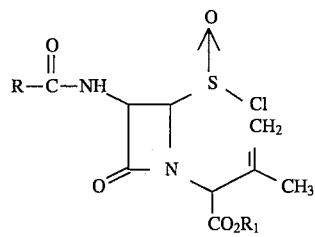

wherein R is hydrogen; $C_1$–$C_3$ alkyl; halomethyl; cyanomethyl;

phenyl; substituted phenyl wherein the substituent is selected from halo, alkyl, alkoxy, protected hydroxy, nitro, cyano or trifluoromethyl; phenoxy, benzyloxy or substituted benzyl wherein the substituent is selected from halo, alkyl, alkoxy, protected hydroxy, nitro, cyano or trifluoromethyl;

a group of the formula $R_2$—O— where $R_2$ is t-butyl, 2,2,2-trichloroethyl, benzyl or substituted benzyl wherein the substituent is selected from methoxy or nitro;

a group of the formula $R_3$—(O)$_n$—$CH_2$ wherein $R_3$ is phenyl or substituted phenyl with the substituent selected from halo, alkyl, alkoxy, protected hydroxy, nitro, cyano, trifluoromethyl, 2-thienyl, 3-thienyl, 2-furyl, 3-furyl or 1,4-cyclohexadienyl, and n is 0 or 1; or a substituted aryl alkyl group of formula

wherein $R_4$ has the same meaning as $R_3$ defined above and W is a protected hydroxy or protected amino group; and $R_1$ is a carboxylic acid protecting group selected from the group consisting of $C_1$–$C_4$ alkyl; 2,2,2-trihalo alkyl, wherein the alkyl is not methyl; benzyl; phenacyl; halo substituted phenacyl; substituted benzyl wherein the substituted benzyl is selected from p-nitrobenzyl or benzhydryl, which comprises reacting a penicillin sulfoxide ester of the general formula

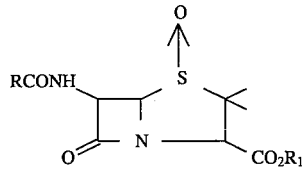

wherein R and $R_1$ have the meanings defined herein with an N-chloro-halogenating agent in an inert organic solvent at a temperature of from 70° C. to 150° C., the reaction being conducted in the presence of an acid scavenging agent selected from phosphate or hydrogen phosphate bound to an alkali metal, alkaline earth metal, ammonium ion, or quaternary ammonium ion or mixtures of phosphate or hydrogen phosphate bound to an alkali metal, alkaline earth metal, ammonium ion or quaternary ammonium ion.

2. A method as claimed in claim 1 wherein $R_1$ is selected from the group consisting of methyl, ethyl, n-propyl, isopropyl, n-butyl, isobutyl, sec-butyl, t-butyl, 2,2,2-trichloroethyl, 2,2,2-tribromoethyl, benzyl, p-nitrobenzyl, benzhydryl, and p-chlorophenacyl.

3. A method as claimed in claim 1 wherein $R_1$ is selected from the group consisting of methyl, benzyl, ρ-nitrobenzyl, benzhydryl and 2,2,2-trichloroethyl.

4. A method as claimed in claim 1 wherein said phosphate or hydrogen phosphate constituting said acid scavenging agent include orthophosphates, metaphosphates and polyphosphates of said metals.

5. A method as claimed in claim 1 wherein said acid scavenging agent is an alkali metal phosphate or hydrogen phosphate with said alkali metal being selected from lithium, sodium, potassium or cesium.

6. A method as claimed in claim 1 wherein said acid scavenging agent is an alkaline earth metal phosphate or hydrogen phosphate with said alkaline earth metal being selected from magnesium, calcium, strontium or barium.

7. A method as claimed in claim 1 wherein said acid scavenging agent is a quaternary ammonium phosphate or quaternary ammonium hydrogen phosphate represented by one of the following structures:

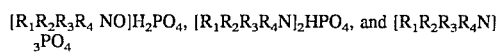

wherein each of $R_1$, $R_2$, $R_3$ and $R_4$ is hydrogen, an alkyl group, or benzyl.

8. A method as claimed in claim 1 wherein said N-chlorohalogenating agent is selected from N-chloro urea, N-chloro amide, N-chloro urethane, N-chloro sulfonamide, N-chlorosulfinimide, N-chloroimide, N-chloro succinimide or N-chlorophthalimide.

9. A method as claimed in claim 1 wherein the organic solvent is selected from the group consisting of benzene, toluene, cyclohexane, n-hexane, ethyl benzene, xylene, mesitylene, dichloromethane, diphenyl ether, tetrahydrofuran, carbon tetrachloride, chloroform, and 1,1,2 trichloroethane or any aprotic solvent which does not react with either the starting reactants or the product of the reaction.

10. A method as claimed in claim 9 wherein the solvent is selected from the group consisting of benzene, toluene, cyclohexane, n-hexane, ethyl benzene, xylene, mesitylene, dichloromethane, diphenyl ether, tetrahydrofuran, carbon tetrachloride, chloroform, and 1,1,2 trichloroethane.

11. A method as claimed in claim 1 wherein said reaction is conducted at a temperature of from 100° C. to 115° C.

12. A method as claimed in claim 1 wherein said penicillin sulfoxide ester and said N-chlorohalogenating agent are in a molar ratio of between 1 to 1.5.

13. A method for the preparation of 2-chloro sulfinyl azetidin-4-one of the formula:

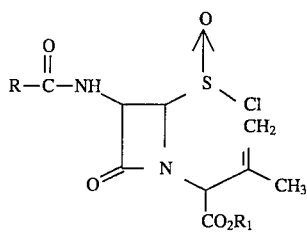

wherein R is:

hydrogen; $C_1$–$C_3$ alkyl; halomethyl; cyanomethyl; phenyl, phenoxy, benzyl, substituted phenyl wherein the substituted phenyl is halophenyl, or substituted benzyl wherein the substituent is selected from methoxy or nitro;

a group of the formula $R_2$—O— wherein $R_2$ is t-butyl, 2,2,2-trichloroethyl, benzyl or substituted benzyl wherein the substituent group is selected from methoxy or nitro;

a group of the formula $R_3$—(O)$_n$—CH$_2$ wherein $R_3$ is phenyl or substituted phenyl wherein the substituted phenyl is halophenyl; and n is 0 or 1; and $R_1$ is a carboxylic acid protecting group selected from the group consisting of $C_1$–$C_4$ alkyl; 2,2,2-trihalo alkyl wherein the alkyl is not methyl; benzyl; substituted benzyl wherein the substituted benzyl is selected from ρ-nitrobenzyl, ρ-methoxybenzyl, phenacyl, halo substituted phenacyl or benzhydryl;

which comprises reacting a penicillin sulfoxide ester of the general formula

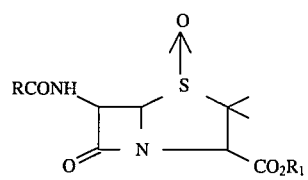

wherein R and $R_1$ are as defined herein with an N-chloro halogenating agent in a molar ratio of 1 to 1.5 in an inert organic solvent selected from the group consisting of benzene, toluene, cyclohexane, n-hexane, ethyl benzene, xylene, mesitylene, dichloromethane, diphenyl ether, tetrahydrofuran, carbon tetrachloride, chloroform, 1,1,2-trichloroethane or any aprotic solvent which does not react with either the starting reactants or the product of the reaction, at a temperature of from 100° C. to 115° C., the reaction being conducted in the presence of an acid scavenging agent selected from a phosphate or hydrogen phosphate bound to an alkali metal, alkaline earth metal, ammonium ion, quaternary ammonium ion or mixtures of phosphate or hydrogen phosphate bound to an alkali metal, alkaline earth metal, or ammonium ion or quaternary ammonium ion.

14. A method as claimed in claim 13 wherein $R_1$ is selected from the group consisting of methyl, ethyl, n-propyl, isopropyl, n-butyl, isobutyl, sec-butyl, t-butyl, 2,2,2-trichloroethyl, 2,2,2-tribromoethyl, benzyl, ρ-nitrobenzyl, ρ-methoxybenzyl, benzhydryl, phenacyl, ρ-chlorophenacyl and ρ-bromophenacyl.

15. A method according to claim 13 wherein $R_1$ is selected from methyl, benzyl, ρ-nitrobenzyl, ρ-methoxybenzyl, benzhydryl or 2,2,2-trichloroethyl.

16. A method as claimed in claim 13 wherein said reaction is carried out in an excess of said N-chlorohalogenating agent.

17. A method as claimed in claim 13 wherein the molar ratio of said N-chlorohalogenating agent to said acid scavenging agent is from 0.3 to 15.

18. A method as claimed in claim 17 wherein the molar ratio of said N-chlorohalogenating agent to said acid scavenging agent is from 10 to 13.

19. A process for the synthesis of a 3-exomethylene cepham sulfoxide ester of the formula

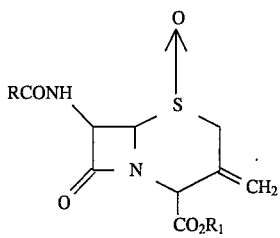

wherein R is:

hydrogen; $C_1$–$C_3$ alkyl; halomethyl; cyanomethyl; phenyl; phenoxy, benzyl, substituted phenyl wherein the substituted phenyl is halophenyl, or substituted benzyl wherein the substituent is selected from methoxy or nitro;

a group of the formula $R_2$—O— wherein $R_2$ is t-butyl, 2,2,2-trichloroethyl, benzyl or substituted benzyl wherein the substituent group is selected from methoxy or nitro;

a group of the formula $R_3$—(O)$_n$—$CH_2$ wherein $R_3$ is phenyl or substituted phenyl wherein the substituted phenyl is halophenyl; and n is 0 or 1; and $R_1$ is a carboxylic acid protecting group selected from the group consisting of $C_1$–$C_4$ alkyl; 2,2,2-trihalo alkyl wherein the alkyl is not methyl; benzyl; substituted benzyl wherein the substituted benzyl is selected from ρ-nitrobenzyl, ρ-methoxy benzyl, phenacyl, halo substituted phenacyl or benzhydryl; which comprises reacting a penicillin sulfoxide ester of the formula

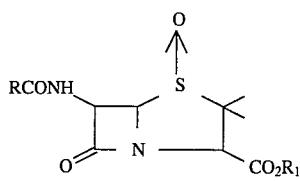

wherein R and $R_1$ are as defined herein
with an N-chloro halogenating agent in an inert organic solvent at a temperature of from 70° C. to 150° C., the reaction being conducted in the presence of an acid scavenging agent selected from an alkali metal, alkaline earth metal, ammonium, or quaternary ammonium phosphate or hydrogen phosphate or a mixed alkali metal, alkaline earth metal, ammonium ion or quaternary ammonium phosphate or hydrogen phosphate and recovering the 2-chloro sulfinyl azetidin-4-one thus prepared and cyclizing it to a 3-exomethylene cepham sulfoxide ester.

20. A method as claimed in claim 19 wherein $R_1$ is selected from the group consisting of methyl, ethyl, n-propyl, isopropyl, n-butyl, isobutyl, sec-butyl, t-butyl, 2,2,2-trichloroethyl, 2,2,2-tribromoethyl, benzyl, ρ-nitrobenzyl, ρ-methoxybenzyl, benzhydryl, phenacyl, ρ-chlorophenacyl and ρ-bromophenacyl.

21. A method as claimed in claim 19 wherein $R_1$ is selected from the group consisting of methyl, benzyl, ρ-nitrobenzyl, ρ-methoxybenzyl, benzhydryl and 2,2,2-trichloroethyl.

22. A process as claimed in claim 19 wherein said cyclization is effected by reacting recovered 2-chloro sulfinyl azetidin-4-one with a Friedel-Crafts catalyst.

23. A process as claimed in claim 22 wherein said Friedel-Crafts catalyst is a Lewis acid selected from stannic chloride, ferric chloride or zinc chloride.

* * * * *